United States Patent [19]
Matsui et al.

[11] Patent Number: 5,538,973
[45] Date of Patent: Jul. 23, 1996

[54] IMIDAZOLE DERIVATIVE, PHARMACEUTICAL USE THEREOF, AND INTERMEDIATE THEREFOR

[75] Inventors: Hiroshi Matsui, Nara; Shoji Kamiya, Kyoto; Hiroaki Shirahase, Nagaokakyo; Shohei Nakamura, Kyoto, all of Japan

[73] Assignee: Kyoto Pharmaceutical Industries, Ltd., Kyoto, Japan

[21] Appl. No.: 393,042

[22] Filed: Feb. 23, 1995

Related U.S. Application Data

[63] Continuation of Ser. No. 142,443, filed as PCT/JP93/00378, Mar. 26, 1993, abandoned.

[30] Foreign Application Priority Data

Mar. 27, 1992 [JP] Japan .................. 4-102071

[51] Int. Cl.$^6$ ............... A61K 31/495; A61K 31/445; C07D 401/14; C07D 403/14
[52] U.S. Cl. ............... 514/253; 514/254; 514/323; 544/370; 546/201; 548/312.1
[58] Field of Search .................. 544/370; 514/253, 514/254, 323; 546/201

[56] References Cited

U.S. PATENT DOCUMENTS

| | | | |
|---|---|---|---|
| 4,139,634 | 2/1979 | Pigerol et al. | 546/201 |
| 4,217,357 | 8/1980 | Cross et al. | 514/397 |
| 4,273,782 | 6/1981 | Cross et al. | 514/397 |
| 4,451,472 | 5/1984 | Cross et al. | 514/339 |
| 4,731,363 | 3/1988 | Hamilton et al. | 514/256 |
| 5,324,737 | 6/1994 | D'Ambra et al. | 546/201 |

FOREIGN PATENT DOCUMENTS

| | | |
|---|---|---|
| 0050957 | 5/1982 | European Pat. Off. |
| 0073663 | 3/1983 | European Pat. Off. |
| 0429257 | 5/1991 | European Pat. Off. |
| 0488532 | 6/1992 | European Pat. Off. |
| 132569 | 10/1979 | Japan |

OTHER PUBLICATIONS

Bhat et al, *J. Allergy Clin. Immunol.* 58, pp. 647–656 (1976).
Iwamoto et al, *Journal of Asthma*, 25, pp. 117–124 (1988).
Salmon in *Advances in Drug Research* Edited by Bernard Testa, vol. 15, pp. 111–167 (1986).
Lianos et al, *J. Clin. Invest.* 72, pp. 1439–1448 (1983).
Suzuki et al, *Neurological Research*, 11 pp. 79–88 (1989).
Japio Abstract for JP 3–7281, Jan. 14, 1991.
*Advanced Organic Chemistry* (2nd Ed.) by Jerry March (McGraw–Hill) pp. 349–353 (1977).

Primary Examiner—Emily Bernhardt
Attorney, Agent, or Firm—Sughrue, Mion, Zinn, Macpeak & Seas

[57] ABSTRACT

An imidazole derivative of the formula (I)

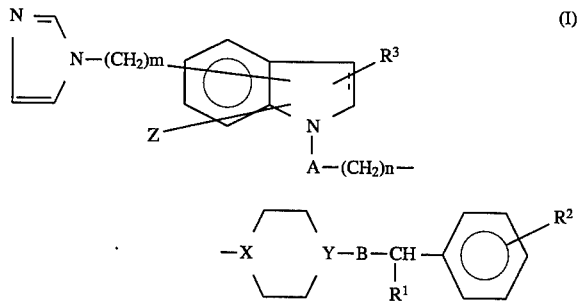

wherein each symbol is as defined in the specification, or a pharmacologically acceptable salt thereof is described. A method for producing the compound or its salt, and its pharmaceutical use, particularly as an agent for the prophylaxis and treatment of the diseases induced by thromboxane $A_2$ or histamine are described. Also, compounds of the formula (II) and (IV)

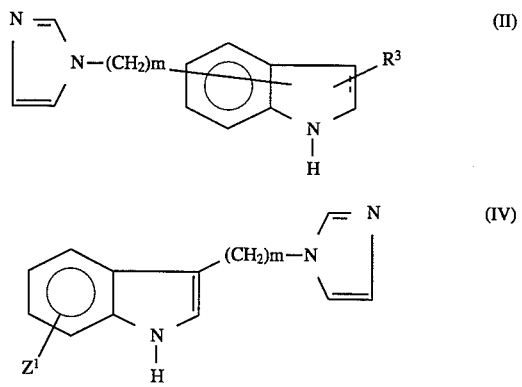

wherein each symbol is as defined in the specification are described. The imidazole derivative and its parmacologically acceptable salt are useful as agents for the prophylaxis and treatment of the diseases induced by thromboxane $A_2$ or histamine, and the intermediate compounds (II) and (IV) are novel compounds.

4 Claims, No Drawings

IMIDAZOLE DERIVATIVE, PHARMACEUTICAL USE THEREOF, AND INTERMEDIATE THEREFOR

This is a Continuation of application Ser. No. 08/142,443, filed as PCT/JP93/00378, Mar. 26, 1993, now abandoned.

TECHNICAL FIELD

The present invention relates to a novel imidazole derivative and its pharmacologically acceptable salt which are useful as pharmaceuticals, etc., production thereof, and an agent for the prophylaxis and treatment of the diseases induced by thromboxane $A_2$ or histamine, which comprises the derivative or its salt as an active ingredient. The present invention also relates to a compound obtained in the process of producing said imidazole derivative, which is useful as an intermediate.

BACKGROUND ART

Imidazole derivatives have been conventionally known to show pharmacological actions such as inhibitory action on the synthesis of thromboxane $A_2$, and thereby-induced blood platelet aggregation-inhibitory action and vasodilative action, and also known to be useful for the prophylaxis and treatment of the circulatory organ disorders, such as thrombosis, cerebral apoplexy, and so on, as well as allergy. Yet, these derivatives have been studied in terms of pharmacological action for relatively a short time, and there is a great expectation for the application of the derivatives as pharmaceuticals and toward the creation of new drugs.

At present, a compound of the formula (V)

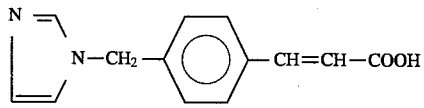

(V)

is being used at the clinical situations as an imidazole derivative preparation for the prophylaxis and treatment of cerebrovascular spasm. Moreover, the effectiveness of the imidazole derivative against bronchial asthma has been recently confirmed, and its novel use as an agent for treating asthma has received increasing attention.

Accordingly, an object of the present invention is to provide a novel, low-toxic imidazole derivative or a pharmacologically acceptable salt thereof which exhibits extremely superior pharmacological activities, namely, pharmacological actions such as inhibitory action on the synthesis of thromboxane $A_2$; thereby-induced blood platelet aggregation-inhibitory action and vasodilative action; antihistaminic action; and inhibitory action on respiratory tract contraction caused by histamine or leukotriene.

Another object of the present invention is to provide an agent for the prophylaxis and treatment of the diseases induced by thromboxane $A_2$ or histamine, namely, an agent for the prophylaxis and treatment of thrombosis, cerebral apoplexy, ischemic cerebral circulatory disorders angina pectoris myocardial infarction, nephritis, allergy, asthma, and so on.

Still another object of the present invention is to provide a compound useful as an intermediate for the production of said imidazole derivatives.

DISCLOSURE OF THE INVENTION

The present inventors have taken note of the superior pharmacological actions of the imidazole derivative, and intensively studied so as to obtain an imidazole derivative exhibiting particularly high antiallergic activity, and now found that a compound of the following formula (I) wherein specific substituents have been introduced into the indole ring or a pharmaceutically acceptable salt thereof shows inhibitory action on the synthesis of thromboxane $A_2$, and thereby-induced blood platelet aggregation-inhibitory action and vasodilative action, as well as antihistaminic action and superior inhibitory action on respiratory tract contraction caused by histamine or leukotriene.

While there has been suggested the effectiveness of known imidazole derivatives against bronchial asthma, the imidazole derivative and its pharmaceutically acceptable salt of the present invention are considered to be extremely effective as an antiasthma and an antiallergy in view of their antihistaminic action, antileukotriene action and the absence of anticholine action to make sputum viscous and expectoration difficult. As a result of the study, the present inventors have confirmed that said compound and a composition containing said compound as an active ingredient are, besides the known pharmaceutical use, usable as an extremely effective agent for the prophylaxis and treatment of bronchial asthma, allergy, and so on, and intensive study thereafter resulted in the completion of the present invention.

That is, the present invention relates to an imidazole derivative of the formula (I)

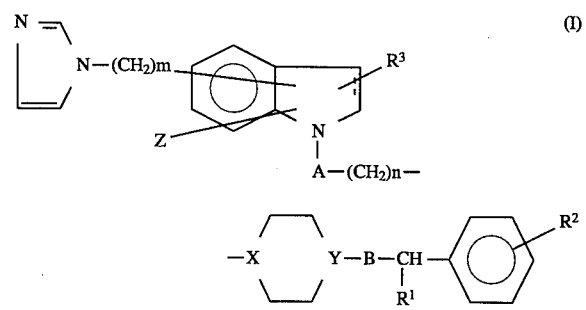

(I)

wherein $R^1$ is hydrogen atom or aryl, $R^2$ is hydrogen atom, halogen, lower alkyl, or lower alkoxy, $R^3$ is hydrogen atom or lower alkyl, A is a direct bond, —CO—, —CH$_2$CO—, —CONH—, —COCH$_2$O—, or alkyleneoxy, B is a direct bond, —O—, alkylene, or alkyleneoxy, X and Y are both nitrogen atoms or either of them is nitrogen atom and the other is CH, Z is hydrogen atom, carboxyl, or esterified carboxyl, m and n are 0 or an integer of 1–4, and the broken line means a single bond or double bond, or a pharmacologically acceptable salt thereof.

Also, the present invention relates to a method for producing the imidazole derivative as claimed in claim 1 or its salt, which comprises Method 1: Reacting a Compound of the Formula (VI)

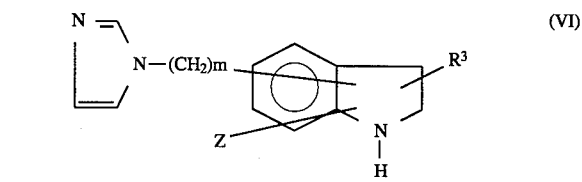

(VI)

wherein $R^3$, Z, and m are as defined above, with a compound of the formula (VII)

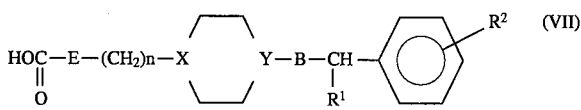

wherein E is a direct bond or methyleneoxy, and $R^1$, $R^2$, B, X, Y, and n are as defined above, or Method 2: Reacting a Compound of the Formula (VI) Above with a Compound of the Formula (VIII)

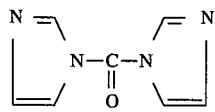

or a compound of the formula (IX)

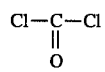

to obtain an N-carbonyl derivative and reacting this N-carbonyl derivative with a compound of the formula (X)

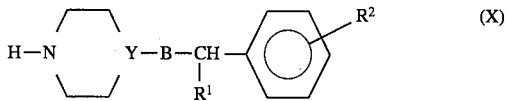

wherein $R^1$, $R^2$, B, and Y are as defined above, or reacting said N-carbonyl derivative with a compound of the formula (XI)

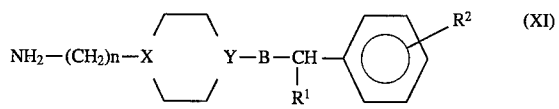

wherein $R^1$, $R^2$, B, X, Y, and n are as defined above, or

Method 3: Reacting a Compound of the Formula (XII)

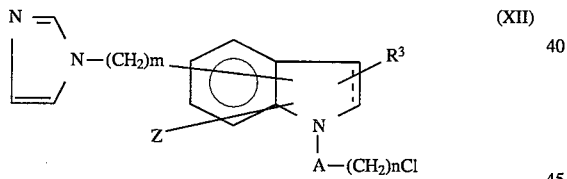

wherein Z is an esterified carboxyl, and $R^3$, A, n, m, and the broken line are as defined above, with a compound of the formula (XIII)

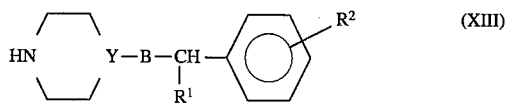

wherein $R^1$, $R^2$, B, and Y are as defined above, in the presence of a base, or Method 4: Reacting a Compound of the Formula (XIV)

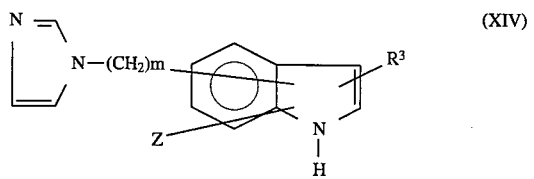

wherein Z is an esterified carboxyl, and $R^3$ and m are as defined above, with a compound of the formula (XV)

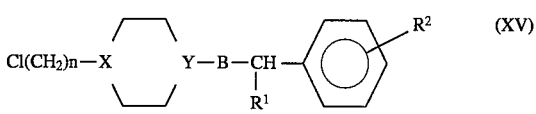

wherein $R^1$, $R^2$, B, X, Y, and n are as defined above, in the presence of a base, or Method 5:1 Further Hydrolyzing the Compound Produced by the Method 3 or 4.

The present invention also relates to a pharmaceutical composition containing said imidazole derivative (I) or its pharmacologically acceptable salt and pharmacologically acceptable carriers, and an agent for the prophylaxis and treatment of the diseases induced by thromboxane $A_2$ or histamine.

Furthermore, the present invention relates to an intermediate for the production of the aforementioned imidazole derivative, namely, a novel compound of the formula (II)

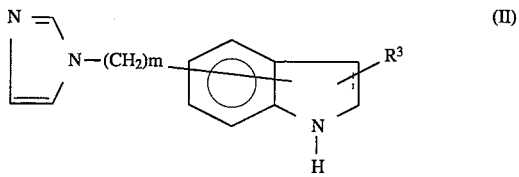

wherein $R^3$ is hydrogen atom or lower alkyl. In the formula, a group of the formula (III)

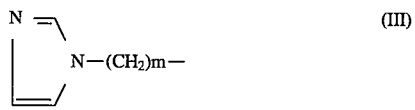

wherein m is 0 or an integer of 1–4, is substituted at the 3- or 5-position of the indole ring or indoline ring of the compound (II), and the broken line means a single bond or double bond, provided that when the compound has an indole ring, m is 0, 2, 3, or 4; and a novel compound of the formula (IV)

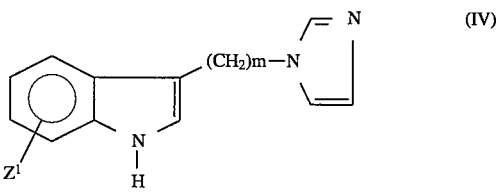

wherein $Z^1$ is carboxyl or an esterified carboxyl which is substituted at the 5- or 6-position of the indole ring, and m is an integer of 1 or 2.

In the present specification, each symbol and group stand for the following and are exemplified by the following.

As regards $R^1$, aryl is an aromatic hydrocarbon such as phenyl, tolyl, or xylyl and may have a substituent, such as halogen (e.g. chloro, fluoro), nitro, or alkoxy (e.g. methoxy, ethoxy) on the benzene ring. Examples of the aryl include phenyl, chlorophenyl, fluorophenyl, nitrophenyl, methoxyphenyl, tolyl, and xylyl, with preference given to phenyl.

As regards $R^2$ and $R^3$, lower alkyl may be straight or branched and is preferably an alkyl having 1 to 4 carbon atoms such as methyl, ethyl, propyl, iso-propyl, n-butyl, iso-butyl, or t-butyl, with particular preference given to an alkyl having 1 to 3 carbon atoms.

As regards $R^2$, lower alkoxy may be straight or branched and is preferably an alkoxy having 1 to 4 carbon atoms such as methoxy, ethoxy, propoxy, iso-propoxy, butoxy, iso-butoxy, sec-butoxy, or tert-butoxy, with particular preference given to an alkoxy having 1 to 3 carbon atoms.

As regards $R^2$, halogen is exemplified by fluorine, chlorine, bromine, and iodine, with preference given to fluorine and chlorine.

As regards A and B, the alkylene moiety of alkylene and alkyleneoxy is straight or branched and is exemplified by an alkylene moiety having 1 to 5 carbon atoms such as methylene, ethylene, trimethylene, tetramethylene, methylmethylene, ethylethylene, dimethylmethylene, or dimethylethylene, with preference given to a straight chain alkylene having 1 to 4 carbon atoms. As alkyleneoxy, preferred are ethyleneoxy and methyleneoxy.

As regards Z and $Z^1$, the ester residue when carboxyl has been esterified is alkyloxy having 1 to 4 carbon atoms which may be straight or branched. Examples of the alkyloxy include methoxy, ethoxy, propoxy, isopropoxy, butoxy, isobutoxy, sec-butoxy, tert-butoxy, pentyloxy, and hexyloxy, with preference given to methoxy and ethoxy.

Examples of the pharmacologically acceptable salt of the imidazole derivative (I) of the present invention include acid addition salts with inorganic acids such as hydrochloric acid, hydrobromic acid, and sulfuric acid, and those with organic acids such as acetic acid, oxalic acid, fumaric acid, maleic acid, citric acid, tartaric acid, methanesulfonic acid, and toluenesulfonic acid; salts with metals such as sodium, potassium, calcium, and aluminum; and salts with amino acids such as glycine and alanine. By converting to such salts, absorption from the digestive tract can be enhanced, and formulation into preparations can be made easier. Preferable acid addition salts and metal salts include salts with oxalic acid, maleic acid, methanesulfonic acid, hydrochloric acid, acetic acid, sodium, and potassium. The most preferred are salts with hydrochloric acid, oxalic acid, and sodium. Such acid salt or metal salt is generally contained in a ratio of 1–3 moles per mole of the imidazole derivative (I).

The imidazole derivative (I) and its pharmacologically acceptable salt can be produced, for example, by the following methods.

Method 1

A compound of the formula (I) wherein A is —CO— or —COCH$_2$O— is produced by the following method. That is, a compound of the formula (VI)

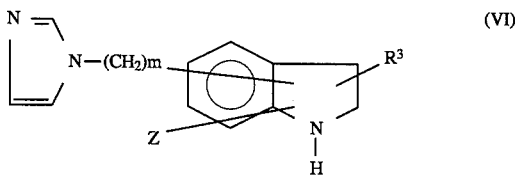
(VI)

wherein $R^3$, Z, and m are as defined above, is reacted with a compound of the formula (VII)

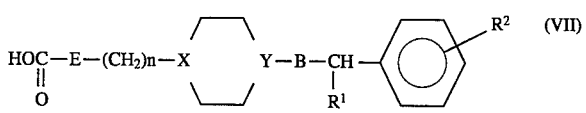
(VII)

wherein E is a direct bond or methyleneoxy, and $R^1$, $R^2$, B, X, Y, and n are as defined above.

The compound (VII) is used in the present reaction as a free carboxylic acid or its reactive derivative. That is, it is subjected to the acylation as a free acid, or a salt with sodium, potassium, calcium, triethylamino, or pyridine, or a reactive derivative such as acid halide thereof (e.g. acid chloride, acid bromide), acid anhydride, mixed acid anhydride [e.g. substituted phosphoric acid (dialkylphosphoric acid), alkylcarbonic acid (monoethylcarbonic acid)], activated amide (e.g. amide with imidazole), or ester (e.g. cyanomethyl ester, 4-nitrophenyl ester).

In this reaction, when the compound (VII) is used as a free acid or a salt, the reaction is preferably carried out in the presence of a condensing agent. Examples of the condensing agent include dehydrating agents such as N,N-di-substituted carbodiimides (e.g. N,N-dicyclohexylcarbodiimide), carbodiimide compounds [e.g. 1-ethyl-3-(3'-dimethylaminopropyl)carbodiimide, N-cyclohexyl-N'-morpholinoethylcarbodiimide, N-cyclohexyl-N'-(4-diethylaminocyclohexyl)carbodiimide], and azoride compounds (e.g. N,N-carbonyldiimidazole, N,N-thionyldiimidazole). When these condensing agents are used, the reaction is considered to proceed a reactive derivative of the carboxylic acid.

Said reaction preferably proceeds in a suitable solvent. The solvent may be any insofar as it does not adversely affect the reaction, and is exemplified by alkanols such as methanol, ethanol, propanol, isopropanol, and ethylene glycol, ethers such as ethyl ether, dioxane, and tetrahydrofuran, ketones such as acetone and methyl ethyl ketone, water, pyridine, N,N-dimethylformamide, dimethyl sulfoxide, acetic acid, benzene, acetonitrile, chloroform, dichloromethane, and ethyl acetate. The reaction temperature is generally from about –20° C. to about 120° C., preferably from about 10° C. to about 40° C. The reaction time is usually from 1 to 24 hours until the reaction ends. The compound (VII) is preferably used in an amount of 0.8–1.5 moles per mole of the compound (VI).

Method 2

A compound of the formula (I) wherein n is 0, A is —CO—, and X is nitrogen atom, and a compound of the formula (I) wherein n is 0–4 and A is —CONH— are produced, for example, by the following method.

That is, the aforementioned compound (VI) is reacted with a compound of the formula (VIII)

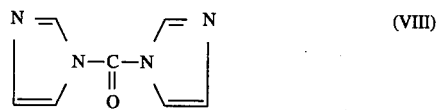
(VIII)

or a compound of the formula (IX)

(IX)

to obtain an N-carbonyl derivative and this N-carbonyl derivative is reacted with a compound of the formula (X)

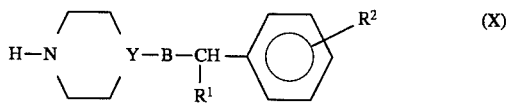
(X)

wherein $R^1$, $R^2$, B, and Y are as defined above, whereby a compound of the formula (I) wherein n is 0, A is —CO—, and X is nitrogen atom is produced. By reacting the aforementioned N-carbonyl derivative with a compound of the formula (XI)

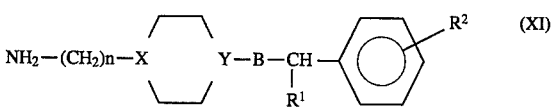
(XI)

wherein $R^1$, $R^2$, B, X, Y, and n are as defined above, a compound of the formula (I) wherein n is 0–4, and A is —CONH— is produced.

Said reaction preferably proceeds in a suitable solvent. The solvent may be any insofar as it does not adversely affect the reaction, and is exemplified by alkanols such as methanol, ethanol, propanol, isopropanol, and ethylene glycol, ethers such as ethyl ether, dioxane, and tetrahydrofuran, ketones such as acetone and methyl ethyl ketone, water, pyridine, N,N-dimethylformamide, dimethyl sulfoxide, acetic acid, benzene, acetonitrile, chloroform, dichloromethane, and ethyl acetate. The reaction temperature is generally from about −20° C. to about 200° C., preferably from about 150° C. to about 180° C. The reaction time is usually from 1 to 18 hours until the reaction ends. When an N-carbonyl derivative is produced, the compound (VIII) or the compound (IX) is preferably used in an amount of 1.1–2.2 moles per mole of the compound (VI). By using the compound (X) or the compound (XI) in an amount of 1.0–1.5 moles per mole of the obtained N-carbonyl derivative, the compound is preferably obtained.

Method 3

A compound of the formula (I) wherein Z is an esterified carboxyl and X is nitrogen atom is produced, for example, by the following method. That is, a compound of the formula (XII)

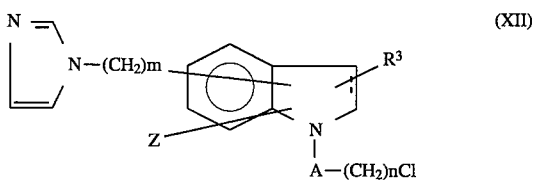

wherein Z is an esterified carboxyl, and $R^3$, A, n, m, and the broken line are as defined above, is reacted with a compound of the formula (XIII)

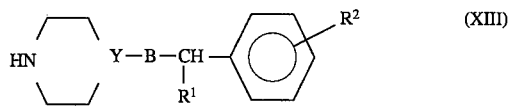

wherein $R^1$, $R^2$, B, and Y are as defined above, in the presence of a base such as sodium hydroxide, potassium hydroxide, potassium carbonate, sodium hydride, pyridine, or triethylamine.

Said reaction preferably proceeds in a suitable solvent. The solvent may be any insofar as it does not adversely affect the reaction, and is exemplified by alkanols such as methanol, ethanol, propanol, isopropanol, and ethylene glycol, ethers such as ethyl ether, dioxane, and tetrahydrofuran, ketones such as acetone and methyl ethyl ketone, water, pyridine, N,N-dimethylformamide, dimethyl sulfoxide, acetic acid, benzene, acetonitrile, chloroform, dichloromethane, and ethyl acetate. The reaction temperature is generally from about 0° C. to about 120° C., preferably from about 10° C. to about 80° C. The reaction time is usually from 1 to 18 hours until the reaction ends. The compound (XIII) is preferably used in an amount of 1.1–1.5 moles per mole of the compound (XII).

Method 4

A compound of the formula (I) having an indole ring, wherein A is a direct bond, Z is an esterified carboxyl produced, for example, by the following method. That is, a compound of the formula (XIV)

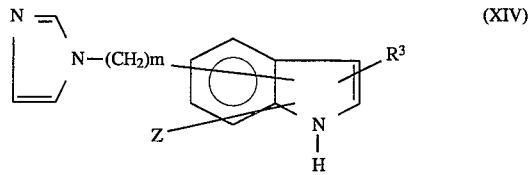

wherein Z is an esterified carboxyl, and $R^3$ and m are as defined above, is reacted with a compound of the formula (XV)

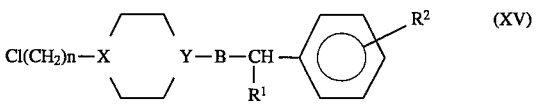

wherein $R^1$, $R^2$, B, X, Y, and n are as defined above, in the presence of a base such as sodium hydroxide, potassium hydroxide, potassium carbonate, sodium hydride, pyridine, or triethylamine.

Said reaction preferably proceeds in a suitable solvent. The solvent may be any insofar as it does not adversely affect the reaction, and is exemplified by alkanols such as methanol, ethanol, propanol, isopropanol, and ethylene glycol, ethers such as ethyl ether, dioxane, and tetrahydrofuran, ketones such as acetone/and methyl ethyl ketone, water, pyridine, N,N-dimethylformamide, dimethyl sulfoxide, acetic acid, benzene, acetonitrile, chloroform, dichloromethane, and ethyl acetate. The reaction temperature is generally from about −20° C. to about 120° C., preferably from about 20° C. to about 80° C. The reaction time is usually from 1 to 18 hours until the reaction ends. The compound XV) is preferably used in an amount of 1.0–1.5 moles per mole of the compound (XIV).

Method 5

A compound wherein Z is carboxyl is produced by hydrolyzing, by a method known per se, the compound wherein Z is an esterified carboxyl, which has been produced by the Method 3 or 4.

Said reaction preferably proceeds in the presence of a suitable acid or alkali. The solvent may be any insofar as it does not adversely affect the reaction, and is exemplified by water, dilute alcohol, acetone, and tetrahydrofuran. The reaction temperature is generally from about 0° C. to about 100° C., preferably from about 10° C. to about 50° C. The reaction time is usually from 5 to 60 minutes until the reaction ends.

A compound of the formula (II)

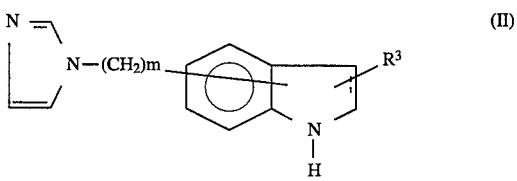

wherein $R^3$, m, the broken line, and the group of the formula (III) are as defined above, and a compound of the formula (IV)

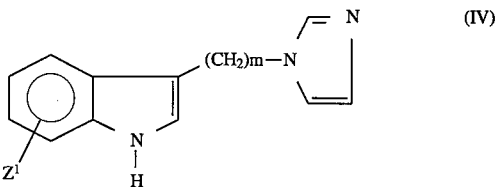

wherein $Z^1$ and m are as defined above, which are obtained during the production of the aforementioned compound (I) are novel compounds.

The novel compounds (II) and (IV) are synthesized, for example, by the following methods.

Method 6

A compound of the formula (II) having an indoline ring, wherein m is 0 and $R^3$ is hydrogen atom, i.e. 5-imidazolylindoline, is obtained, for example, by reacting N-acetyl-5- bromoindoline with imidazole in the presence of copper powder, potassium fluoride, and a suitable base to obtain N-acetyl-5-imidazolylindoline, and hydrolyzing said compound by a known means. Examples of the base include sodium hydroxide, calcium hydroxide, sodium carbonate, potassium carbonate, pyridine, and triethylamine.

Said reaction preferably proceeds in a suitable solvent. The solvent may be any insofar as it does not adversely affect the reaction, and is exemplified by alkanols such as methanol, ethanol, propanol, isobutanol, and ethylene glycol, ethers such as ethyl ether, dioxane, tetrahydrofuran, and ethylene glycol monomethyl ether, water, pyridine, N,N-dimethylformamide, N,N-dimethylacetamide, dimethyl sulfoxide, acetonitrile, and acetone. The reaction temperature is generally from about 10° C. to about 180° C., preferably from about 100° C. to about 150° C. The reaction time is usually from 0.5 to 15 hours until the reaction ends.

Method 7

A compound of the formula (II) having an indoline ring, wherein m is 1 and $R^3$ is hydrogen atom, i.e. 5-imidazolylmethylindoline, is obtained, for example, by chloromethylating N-acetylindoline by a known method to obtain N-acetyl-5-chloromethylindoline, reacting said compound with imidazole in the presence of a suitable base, and hydrolyzing the obtained N-acetyl-5-imidazolylmethylindoline by a known method.

Examples of the base include sodium hydroxide, calcium hydroxide sodium carbonate, potassium carbonate, pyridine, and triethylamine.

Said reaction preferably proceeds in a suitable solvent. The solvent may be any insofar as it does not adversely affect the reaction, and is exemplified by alkanols such as methanol, ethanol, propanol, isobutanol, and ethylene glycol, ethers such as ethyl ether, dioxane, tetrahydrofuran, and ethylene glycol monomethyl ether, water, pyridine, N,N-dimethylformamide, N,N-dimethylacetamide, dimethyl sulfoxide, acetonitrile, and acetone. The reaction temperature is generally from about −10° C. to about 150° C., preferably from about 0° C. to about 60° C. The reaction time is usually from 0.5 to 15 hours until the reaction ends.

Method 8

A compound of the formula (II) having an indole ring of the formula (XIV) is obtained from compound (VI) in the presence of a suitable base.

Examples of the base include sodium hydroxide, calcium hydroxide sodium carbonate, potassium carbonate, sodium hydride, pyridine, and triethylamine.

Said reaction preferably proceeds in a suitable solvent. The solvent may be any insofar as it does not adversely affect the reaction, and is exemplified by alkanols such as methanol, ethanol, propanol, isobutanol, and ethylene glycol, ethers such as ethyl ether, dioxane, tetrahydrofuran, and ethylene glycol monomethyl ether, water, pyridine, N,N-dimethylformamide, N,N-dimethylacetamide, dimethylsulfoxide, acetonitrile, and acetone. The reaction temperature is generally from about −10° C. to about 150° C., preferably from about 0° C. to 80° C. The reaction time is usually from 0.5 to 15 hours until the reaction ends.

Method 9

A compound of the formula (IV) wherein m is 1 can be synthesized by reacting a Mannich base of the formula (XVII)

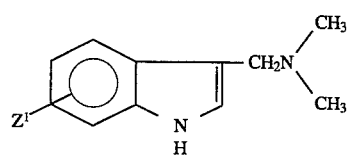

wherein $Z^1$ is as defined above, which is obtained from a compound of the formula (XVI)

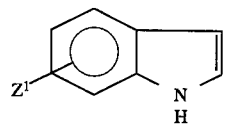

wherein $Z^1$ is as defined above, by Mannich reaction, with imidazole.

Said reaction preferably proceeds in a suitable solvent. Examples of the suitable solvent include xylen, benzene, dimethylacetamide, and toluene. The reaction temperature is generally from about 10° C. to about 150° C., preferably from about 80° C. to about 120° C. The reaction time is usually from 0.5 to 18 hours until the reaction ends. Imidazole is preferably used in an amount of 1 to 10 moles per mole of the Mannich base (XVII).

The imidazole derivative (I) and a pharmacologically acceptable salt thereof can be obtained at an optional purity by a purification means known per se, such as extraction, chromatography, and recrystallization.

The imidazole derivative (I) and its pharmacologically acceptable salt of the present invention show pharmacological actions such as inhibitory action on the synthesis of thromboxane $A_2$ ($TXA_2$); thereby-induced suppressive action on blood platelet aggregation and vasodilative action; antihistaminic action; and suppressive action on respiratory tract contraction caused by histamine or leukotriene (LT), and they have low toxicity. Therefore, they are useful as agents for the prophylaxis and treatment of the diseases caused by $TXA_2$ or histamine, namely, as agents for the prophylaxis and treatment of bronchial asthma, allergy, nephritis, thrombosis, cerebral apoplexy, myocardial infarction, angina pectoris, ischemic cerebral circulatory disorder, and so on.

The imidazole derivative (I) and its pharmacologically acceptable salt of the present invention can be formulated, together with conventional additives, into preparations by a known method in the form of, for example, tablet, sugar-coated tablet, capsule, granule, powder, suppository, or injection which can be administered orally or parenterally.

For oral administration, there may be further added other preferable additives where desired, such as excipients (e.g. starch, lactose, sugar, calcium carbonate, calcium phosphate), binders (e.g. starch, gum arabic, carboxymethylcellulose, hydroxypropylcellulose, crystalline cellulose), lubricants (e.g. magnesium stearate, talc), disintegrators (e.g. calcium carboxymethyl cellulose, talc), and the like.

For parenteral administration, the preparation form of injection or the like is employed, and an aqueous solvent or a nonaqueous solvent such as distilled water for injection, physiological saline, Ringer solution, vegetable oil, propylene glycol, or the like is prepared to give a solution or suspension by a method known per se.

While the dose of the imidazole derivative (I) and its pharmacologically acceptable salt may vary depending on the kind of disease symptom, body weight, age, sex, etc., 1 to 500 mg thereof is generally administered daily to an adult in 1 to 4 times divided doses.

Hereunder follow the results of the pharmacological tests to show the effectiveness of the imidazole derivative (I) and its pharmacologically acceptable salt.

EXPERIMENTAL EXAMPLE 1

Determination of Inhibitory Action on Synthesis of $TXA_2$

Prostaglandin $H_2$ ($PGH_2$) was added as a substrate to an aspirin-treated platelet floating solution, and the mixture was incubated at 37° C. The resultant $TXA_2$ was converted to $TXB_2$, and measured by RIA method. The test drug was added 10 minutes before the addition of $PGH_2$.

EXPERIMENTAL EXAMPLE 2

Determination of Inhibitory Action on Blood Platelet Aggregation

Arachidonic acid aggregation in rich platelet plasma was determined by nephelometry. The test drug was added 1 minute before the addition of the arachidonic acid (0.1 mM).

EXPERIMENTAL EXAMPLE 3

Determination of Antihistaminic Action

A lung parenchymal specimen extracted from guinea pig was hung in a nutritive solution at 37° C., and applied a load of 0.5 g. Contraction caused by histamine under aeration of 95% $O_2$+5% $CO_2$ was recorded isometrically. The inhibition by the test drug with respect to the dose-reaction curve by histamine at $10^{-7}$–$10^{-4}$ was examined.

EXPERIMENTAL EXAMPLE 4

Determination of Inhibitory Action on Contraction of Respiratory Tract

A respiratory tract contraction (histamine, $LTD_4$) was intravenously administered to anesthetized guinea pig, and a change in airway resistance was measured in accordance with Konzett end Roessler method. The test drug was orally administered 1 hour before the administration of the contraction inducing agent.

EXPERIMENTAL EXAMPLE 5

Acute Toxicity

The compound of Example 6 was suspended in a 5% gum arabic solution and orally administered to 5 male ddy mice at 1000 mg/20 ml /kg. No death was observed, and changes in body weight showed no significant difference when compared with a control group. No abnormality was found in the autopsy performed a week later.

The experiments 1–4 described above were conducted using the compounds of Examples 1, 2, 6, 8, 12, 14, 19, 23, 27, 30, 34, and 35 to be mentioned below, compound (V), and Terfenadine, the results of which are shown in Table 1.

TABLE 1

|  | Exp. 1 ($IC_{50}$, μM) | Exp. 2 ($IC_{50}$, μM) | Exp. 3 (%)* | Exp. 4-1 (%)** | Exp. 4-2 (%)** |
|---|---|---|---|---|---|
| Ex. 1 | — | 4.4 | 95 | 100 | 73 |
| Ex. 2 | 1.5 | 4.7 | 66 | 100 | 83 |
| Ex. 6 | 0.4 | 8.1 | 100 | 100 | 75 |
| Ex. 8 | — | 2.1 | 55 | 100 | 87 |
| Ex. 12 | — | 18 | 61 | 100 | 64 |
| Ex. 14 | — | 58 | 45 | 100 | 42 |
| Ex. 19 | — | 21 | 45 | 94 | 40 |
| Ex. 23 | — | 34 | 94 | 94 | 53 |
| Ex. 27 | — | >100 | 58 | 100 | 68 |
| Ex. 30 | — | 9.9 | 100 | 100 | 26 |
| Ex. 34 | — | >100 | 58 | 90 | 31 |
| Ex. 35 | — | 71 | 100 | 100 | 18 |
| Compound (V) | 1.5 | 54 | 8 | 4 | 57 |
| Terfenadine | — | — | 48 | 100 | 27 |

*% at which the test compound ($10^{-5}$ M) suppressed contraction by histamine ($10^{-5}$ M)
**% at which the test compound (30 mg/kg, p.o.) suppressed airway contraction by histamine (4-1) or $LTD_4$ (4-2)

The present invention is more detailedly explained in the following by way of examples, to which the invention is not limited.

EXAMPLE 1

Synthesis of 1-[2-(4-benzhydryl-1-piperazinyl)ethoxyacetyl]-5-(1H-imidazol-1-yl)indoline oxalate 2-(4-Benzhydryl-1-piperazinyl )ethoxy acetate (300 mg) was dissolved in 3 ml of $CH_2Cl_2$, and thereto were added N,N'-dicyclohexylcarbodiimide (228 mg) and 5-(1H-imidazol-1-yl)indoline (204 mg) under ice-cooling. The mixture was stirred at room temperature for 4.5 hours. After the insoluble matters were filtered off, the filtrate was washed with saturated brine, dried over anhydrous sodium sulfate, and concentrated under reduced pressure. The residue obtained (700 mg) was purified by silica gel column chromatography (Daisogel 21 g, elution; $CHCl_3$—$CHCl_3$:MeOH=50:1–25:1) to give 235 mg of an oily substance.

The oily substance (205 mg) was dissolved in ethanol (2 ml), and added with oxalic acid dihydrate (74 mg). Stirring of the mixture afforded crystals which were filtered off to give 194 mg of the title compound, m.p. 131°–133° C. IR (Nujol, vcm$^{-1}$) 3400, 2920, 2850, 1680, 1620, 1540
$^1$H-NMR (DMSO-$d_6$, δ ppm)

2.2–2.9(4H, m, 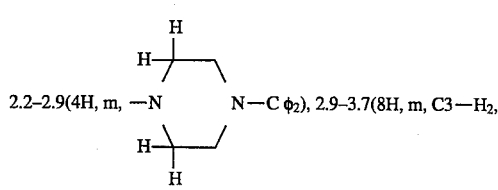), 2.9–3.7(8H, m, C3—H₂,

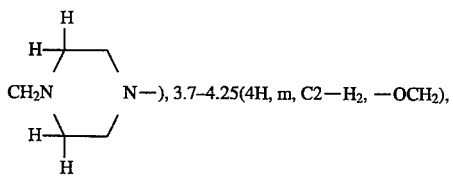), 3.7–4.25(4H, m, C2—H₂, —OCH₂), 4.25–4.7(3H, m, >CH, COCH₂O), 5.27(2H, br-s, oxalic acid), 6.9–7.85(14H, m, phenyl, C4, C6—H, N 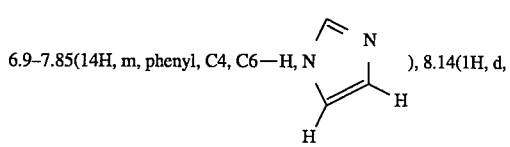), 8.14(1H, d, J=8Hz, C7—H), 8.21(1H, br-s, N 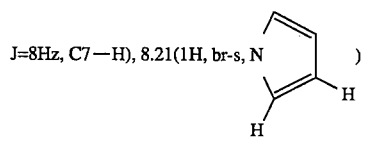)

EXAMPLE 2

Synthesis of 1-{4-[(2-benzhydryloxyethyl)-1-piperazinyl]-carbonyl}- 5-(1H-imidazol-1-yl)indoline oxalate 5-(1H-Imidazol-1-yl)indoline (2 g) was dissolved in tetrahydrofuran (20 ml), and thereto was added 1,1'-carbonyldiimidazole (2.72 g), followed by stirring at room temperature for 30 minutes. The resultant crystals were filtered off and an activated carbonyl compound (2.64 g) was obtained. The activated carbonyl compound (1.50 g) and 1-(2-benzhydryloxyethyl)piperazine (2.40 g) were dissolved in DMF (30 ml), and the mixture was stirred in a sealed reaction tube at 200° C. for 6 hours. The reaction mixture was allowed to cool, added with water, and extracted with ethyl acetate. Then, the extract was washed with a saturated aqueous solution of sodium bicarbonate and saturated brine in order. After drying over anhydrous sodium sulfate, the solvent was distilled away under reduced pressure. The residue was purified by silica gel column chromatography (Daisogel 25 g, elution; CHCl₃—CHCl₃/MeOH=50/1) to give 800 mg of an oily substance.

The oily substance (600 mg) was dissolved in ethanol (6 ml), and added with oxalic acid dihydrate (149 mg). The mixture was heated for dissolution and left standing at room temperature. The resultant crystals were filtered off to give 490 mg of crude crystals. The crude crystals (490 mg) were recrystallized from methanol to give 300 mg of the title compound, m.p. 185.0°–186.0° C. IR (Nujol, vcm⁻¹) 2920, 2850, 1650, 1460 ¹H-NMR (DMSO-d₆, δ ppm)

2.75–4.25(16H, m, 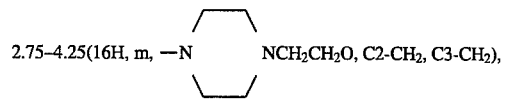 NCH₂CH₂O, C2-CH₂, C3-CH₂), 5.52(1H, s, CH-φ₂), 6.52(2H, s, oxalic acid), 6.95–7.80(5H, m, C₄, C₆, C₇—H, —N 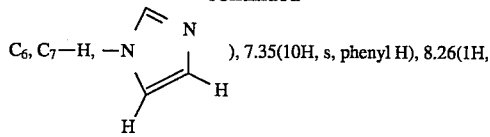), 7.35(10H, s, phenyl H), 8.26(1H, br-s, N 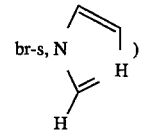)

EXAMPLE 3

Synthesis of 1-[2-(4-benzyl-1-piperizinyl)ethyl]-5-(1H-imidazol-1-yl)-1H-indole oxalate To 5-(1H-imidazol-1-yl)-1H-indole (200 mg) dissolved in DMF (2 ml) was added sodium hydride (53 mg, purity 60%) under ice-cooling, and the mixture was stirred at said temperature for 1 hour. Thereafter, 2-(4-benzyl-1-piperidinyl)ethyl chloride (400 mg) and potassium iodide (83 mg) were added thereto, and the mixture was stirred at room temperature for 18 hours. Water and ethyl acetate were added to the reaction mixture for extraction, followed by washing with saturated brine. After drying over anhydrous sodium sulfate, the solvent was distilled away under reduced pressure. The residue was purified by silica gel column chromatography (Daisogel 20 g, elution; CHCl₃/MeOH= 100/1–50/1) to give 400 mg of an oily substance.

The oily substance (400 mg) was dissolved in ethanol (3 ml), and added with oxalic acid dihydrate (128 mg). After dissolution, the mixture was left standing. The resultant crystals were filtered off to give 400 mg of the title compound.

IR (KBr tablet method, vcm⁻¹) 3400 ¹H-NMR (DMSO-d₆, δ ppm)

1.2–2.0(5H, m, N 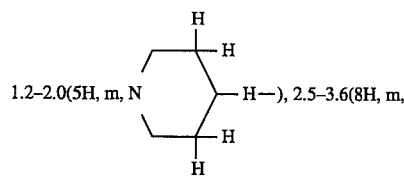 H—), 2.5–3.6(8H, m,

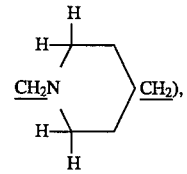), 4.65 (2H, t, J=7 Hz, NCH₂CH₂), 6.5–8.3 (15H, m, indole H, phenyl H, imidazole H, oxalic acid)

EXAMPLE 4

Synthesis of 1-[3-(4-benzhydryl-1-piperazinyl)propyl]-6-ethoxycarbonyl-3-(1H-imidazol-1-ylmethyl)-1H-indole 1-(3-Chloropropyl)-6-ethoxycarbonyl-3-(1H-imidazol-1-ylmethyl)-1H-indole (1.5 g) was dissolved in DMF (15 ml), and thereto were added 1-diphenylmethylpiperazine (1.59 g), potassium carbonate (1.28 g), and potassium iodide (145 mg), followed b stirring at 80° C. for 16 hours. Water and ethyl acetate we added to the reaction mixture for extraction, followed by washing with saturated brine. After drying over anhydrous sodium sulfate, the solvent was distilled away under reduced pressure. The residue was purified by silica gel column chromatography (Daisogel 60 g, elution; CHCl₃/MeOH=10/1) to give 2.4 g of the title compound as an oily substance.

IR (Neat, vcm⁻¹) 1700 ¹H-NMR (CDCl₃, δ ppm) 1.40 (3H, t, J=7 Hz, CH₂CH₃),

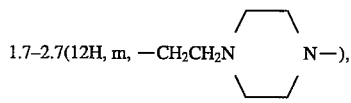

1.7–2.7(12H, m, —CH₂CH₂N  N—), 4.0–4.7 (5H, m, CH₂CH₃, NCH₂CH₂, CH-φ₂), 5.25

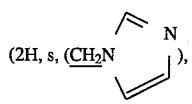

(2H, s, (CH₂N  ), 6.8–8.25 (17H, m, indole H, phenyl H, imidazole H)

EXAMPLE 5

Synthesis of 1-[3-(4-benzhydryl-1-piperazinyl)propyl]-3-(1H-imidazol-1-ylmethyl)-1H-indole-6-carboxylic acid 1-[3-(4-Benzhydryl-1-piperazinyl)propyl]-6-ethoxycarbonyl-3-(1H-imidazol-1-ylmethyl)-1H-indole (2.4 g) as obtained in Example 4 was dissolved in 95% ethanol (25 ml), and thereto was added sodium hydroxide (854 mg), followed by stirring at 70° C. for 2 hours. The solvent was distilled away under reduced pressure. Ethyl acetate and water were added to the residue, and the water layer was purified with HP-21 column to give 700 mg of the sodium salt of the title compound.

IR (Nujol, vcm⁻¹) 1580 ¹H-NMR (DMSO-d₆, δ ppm) 1.5–2.6

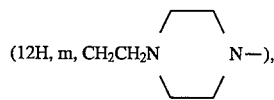

(12H, m, CH₂CH₂N  N—), 4.25 (3H, br, NCH₂CH₂—, CHφ₂), 5.30

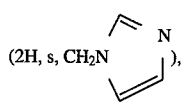

(2H, s, CH₂N  ), 6.7–8.0 (17H, m, indole H, phenyl H, imidazole H)

EXAMPLE 6

Synthesis of 1-[3-(4-benzhydryl-1-piperazinyl)propyl]-5-(1H-imidazol-1-ylmethyl)-1H-indole-2-carboxylic acid trihydrochloride (1) 1-(3-Chloropropyl)-2-ethoxycarbonyl-5-(1H-imidazol-1-ylmethyl)-1H-indole 2-Ethoxycarbonyl-5-(1H-imidazol-1-ylmethyl)-1H-indole (1.00 g) was dissolved in DMF (10 ml), and thereto was added sodium hydride (156 mg, purity 60%) under ice-cooling, followed by stirring at room temperature for 1 hour. Thereto was added 1-bromo-3-chloropropane (0.39 ml), and the mixture was stirred for 1.5 hours. 1-Bromo-3-chloropropane (0.20 ml) was added again, and the mixture was stirred at room temperature for 16 hours. Water and ethyl acetate were added to the reaction mixture for extraction, followed by washing with saturated brine. After drying over anhydrous sodium sulfate, the solvent was distilled away under reduced pressure. The residue was purified by silica gel column chromatography (Daisogel 15 g, elution; CHCl₃—CHCl₃/MeOH=50/1–30/1) to give 1.26 g of an oily substance (1). IR (Neat, vcm⁻¹) 1710, 1700, 1520, 1470 ¹H-NMR (CDCl₃, δ ppm) 1.40 (3H, t, J=6.6 Hz, CH₂CH₃), 2.29 (2H, m, CH₂CH₂Cl), 3.63 (2H, t, J=6.0 Hz, CH₂Cl), 4.38 (2H, quart, J=6.6 Hz, CH₂CH₃), 4.72 (2H, t, J=6.0 Hz, NCH₂), 5.20 (2H, s, C5—CH₂), 6.70–7.85 (7H, indole H, imidazole H)

(2) 1-[3-(4-Benzhydryl-1-piperazinyl)propyl]-2-ethoxycarbonyl-5-(1H-imidazol-1-ylmethyl)-1H-indole The compound (550 mg) as obtained in Example 6 (1) was dissolved in DMF (6 ml), and thereto were added 1-diphenylmethylpiperazine (602 mg), potassium carbonate (330 mg), and sodium iodide (358 mg), followed by stirring at 80° C. for 2 hours. Water and ethyl acetate were added to the reaction mixture for extraction, followed by washing with saturated brine. After drying over anhydrous sodium sulfate, the solvent was distilled away under reduced pressure. The residue was purified by silica gel column chromatography (Daisogel 20 g, elution; CHCl₃/MeOH=50/1) to give 355 mg of an oily substance (2).

IR (Neat, vcm⁻¹) 2800, 1710, 1200 ¹H-NMR (CDCl₃, δ ppm) 1.40 (3H, t, J=7 Hz, CH₂CH₃), 1.65–2.7

(4H, m, NCH₂CH₂CH₂N  NCH), 2.45

(8H, s, —N  N—), 4.22 (1H, s, NCH), 4.35 (2H, quart, J=7.2 Hz, CH₂CH₃), 4.60 (2H, s, NCH₂), 5.18 (2H, s, C5—CH₂), 6.75–7.70 (7H, indole H, imidazole H), 7.28 (10H, s, phenyl H) (3) 1-[3-(4-Benzhydryl-1-piperazinyl)propyl]-5-(1H-imidazol-1-ylmethyl)-1H-indole-2-carboxylic acid trihydrochloride The compound (340 mg) as obtained in Example 6 (2) was dissolved in 95% ethanol (10 ml), and thereto was added 2.13N sodium hydroxide (0.85 ml), followed by stirring at 50° C. for 1.5 hours. After cooling, 3N hydrochloric acid solution (1.22 ml) was added to the reaction mixture, and the mixture was stirred at room temperature for 15 minutes. The solvent was distilled away under reduced pressure. Ethanol (99.5%) was added to the residue, insoluble matters were filtered off, and the solvent was distilled away under reduced pressure to give 256 mg of the title compound as a pale brown powder.

IR (Nujol, vcm⁻¹) 1700, 1460, 1380 ¹H-NMR (DMSO-d₆, δ ppm) 1.50–4.40

(12H, m, NCH₂CH₂CH₂N  NCH—), 4.2–4.9 (3H, m, NCH₂, NCH), 5.53 (2H, s, C5—CH₂), 7.0–8.1 (17H, indole H, phenyl H, imidazole H), 9.47 (2H, br-s, oxalic acid)

EXAMPLE 7

A compound of the formula (XVIII)

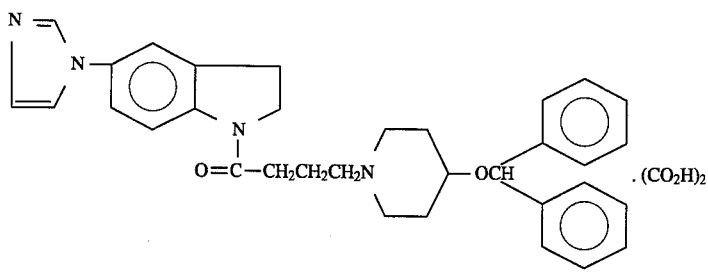

(XVIII)

was produced according to the method of Example 1 above.

IR (KBr tablet method) 3400, 1650, 1600 $^1$H-NMR (DMSO-$d_6$, δ ppm)

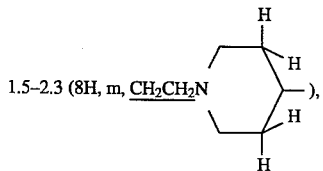

1.5–2.3 (8H, m, CH$_2$CH$_2$N⟨...⟩),

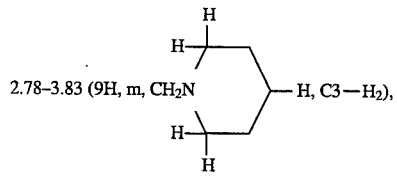

2.78–3.83 (9H, m, CH$_2$N⟨...⟩H, C3—H$_2$), 3.83–4.4 (2H, m, C2-H$_2$), 5.69 (1H, s, CH), 6.1–6.85 (2H, br, oxalic acid), 7.0–7.8 (14H, m, phenyl, C4, C6-H,

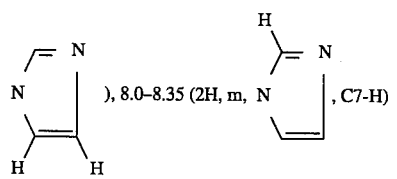

), 8.0–8.35 (2H, m, N⟨...⟩, C7-H)

EXAMPLES 8–16

Compounds of the formula (XIX)

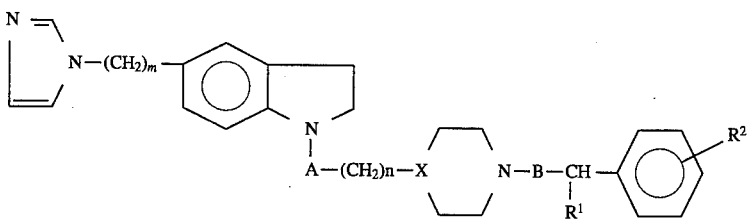

(XIX)

wherein $R^1$, $R^2$, A, B, X, m, and n are as shown in Table 2, were produced according to the methods of Examples 1 and 2 above. The IR and $^1$H-NMR of the obtained compounds are as shown in Table 2.

TABLE 2

| Example | A | B | m, n, X | R¹ | R² | IR(νcm⁻¹) $^1$H-NMR(δppm) |
|---|---|---|---|---|---|---|
| 8 3/2(CO$_2$H)$_2$ | —CO— | —CH$_2$CH$_2$O— | 0, 1, >N— | -φ | —H | IR(Nujol): 3400, 2920, 2850, 1620<br>$^1$H-NMR(DMSO-d$_6$):<br>2.65–3.9(16H, m, CH$_2$N⟨NCH$_2$CH$_2$—⟩, C3-H$_2$)<br>4.19(2H, t, J=8Hz, C2-H$_3$)<br>5.27(br-s, oxalic acid)<br>5.51(1H, s, >CH)<br>7.0–7.77(14H, m, phenyl, C4, C6-H, N⟨imidazole⟩)<br>8.13(1H, d, J=8Hz, C7-H)<br>8.21(1H, s, N⟨imidazole⟩) |
| 9 3/2(CO$_2$H)$_2$ | —CONH— | — | 0, 4, >N— | -φ | —H | IR(Nujol): 2600, 1640, 1455<br>$^1$H-NMR(CDCl$_3$):<br>1.3–1.9(4H, m, C—CH$_2$CH$_2$—C)<br>2.48(8H, s, piperazine)<br>2.48(2H, br-t, —CH$_2$N)<br>3.25(2H, m, NHCH$_2$C—C)<br>3.21(2H, t, J=6Hz, indoline C$_3$—H)<br>3.98(2H, t, J=6Hz, indoline C$_2$—H)<br>4.21(1H, s, NCH)<br>5.10(1H, br-t, NH)<br>7.0–8.2(16H, m, phenyl, imidazole) |
| 10 | —CO— | —CH$_2$CH$_2$O— | 0, 0, >CH— | -φ | —H | IR(Nujol): 3420, 1640, 1600<br>$^1$H-NMR(CDCl$_3$):<br>1.6–2.5(7H, m, OC-piperidine)<br>2.82(2H, t, J=6Hz, >NCH$_2$)<br>2.9–3.3(2H, m, OC-piperidine)<br>3.25(2H, t, J=8Hz, C3-H$_2$)<br>3.64(2H, t, J=6Hz, CH$_2$O)<br>4.22(2H, t, J=8Hz, C2-H$_2$)<br>5.42(1H, s, >CH)<br>7.05–7.55(14H, m, phenyl, C4, C6-H, N⟨imidazole⟩)<br>7.80(1H, s, N⟨imidazole⟩)<br>8.34(1H, d, J=8Hz, C7-H) |

TABLE 2-continued

| Example | A | B | m, n, X | R¹ | R² | IR(vcm⁻¹) ¹H-NMR(δppm) |
|---|---|---|---|---|---|---|
| 11 | —CH₂CO— | —CH₂CH₂O— | 0, 0, >H— | -φ | —H | IR(KBr): 3420, 1640, 1600, 1500<br>¹H-NMR(CDCl₃):<br>2.2–2.94(6H, m, 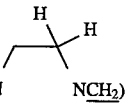)<br>3.20(2H, t, J=8Hz, C3-H₂)<br>3.3–3.85(6H, m, 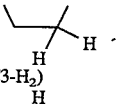)<br>3.93(2H, s, N1—CH₂)<br>4.21(2H, t, J=8Hz, C2-H₂)<br>5.38(1H, s, >CH)<br>6.42(1H, d, J=8Hz, C7-H)<br>6.9–8.05(15H, m, phenyl, C4, C6-H, imidazole) |
| 12 (CO₂H)₂ | —CO— | —CH₂CH₂O— | 1, 0, >N— | -φ | —H | IR(Nujol): 2925, 2850, 1650, 1460<br>¹H-NMR(DMSO-d₆):<br>2.70–4.20(16H, m, 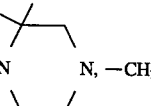)<br>5.22(2H, s, C₆—CH₂)<br>5.52(1H, s, CHφ₂)<br>6.50(2H, s, oxalic acid)<br>6.90–7.65(5H, m, C₄, C₆, C₇-H, 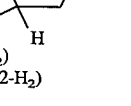)<br>7.35(10H, s, φ₂-H)<br>8.45(1H, br-s, 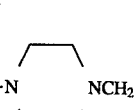) |
| 13 3/2(CO₂H)₂ | —COCH₂O— | — | 1, 2, >N— | -φ | —H | IR(Nujol): 3430, 1640, 1490<br>¹H-NMR(DMSO-d₆):<br>2.3–2.9(4H, m, 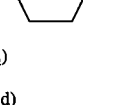)<br>2.9–3.5(8H, m, C3-H₂, 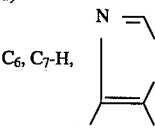)<br>3.65–4.2(4H, m, C2-H₂, —OCH₂)<br>4.2–4.6(3H, m, >CH, COCH₂O)<br>5.20(2H, s, C5-CH₂)<br>6.22(br-s, oxalic acid) |

TABLE 2-continued

| Example | A | B | m, n, X | R¹ | R² | IR(vcm⁻¹) ¹H-NMR(δppm) |
|---|---|---|---|---|---|---|
| | | | | | | 6.9–7.62(14H, m, phenyl, C4, C6-H, 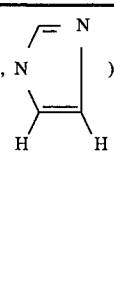) |
| | | | | | | 8.01(1H, d, J=8Hz, C7-H) |
| | | | | | | 8.18(1H, s, 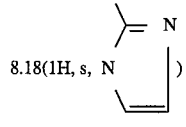) |
| 14 3/2(CO₂H)₂ | —CO— | —CH₂CH₂O— | 1, 1, >N— | -φ | —H | IR(Nujol): 3420, 1620, 1490 ¹H-NMR(DMSO-d₆): |
| | | | | | | 2.68–3.85(16H, m, CH₂N NCH₂CH₂, C3-H₂) |
| | | | | | | 3.9–4.35(2H, m, C2-H₂) 5.26(2H, s, C5-CH₂) 5.53(1H, s, >CH) 5.92(br-s, oxalic acid) |
| | | | | | | 7.0–7.6(14H, m, phenyl, C4, C6-H, 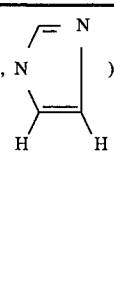) |
| | | | | | | 8.04(1H, d, J=8Hz, C7-H) |
| | | | | | | 8.43(1H, s, 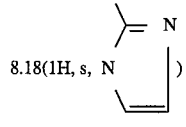) |
| 15 | —CONH— | — | 1, 4, >N— | -φ | —H | IR(Nujol): 2600, 1640, 1455 ¹H-NMR(CDCl₃): 1.3–1.8(4H, m, C—CH₂CH₂—C) 2.48(8H, s, piperazine) 2.48(2H, br-t, —CH₂N) 3.25(2H, m, NHCH₂C—C) 3.21(2H, t, J=6Hz, indoline C₃—H) 3.90(2H, t, J=6Hz, indoline C₂—H) 4.24(1H, s, NCH) 5.01(2H, s, NCH₂φ) 6.8–7.6(15H, m, phenyl, imidazole) 7.91(1H, d, J=8Hz, indoline C₇—H) |
| 16 | —CO— | —CH₂CH₂O— | 1, 0, >CH— | -φ | —H | IR(Nujol): 3420, 1650, 1600, 1490 ¹H-NMR(CDCl₃): |
| | | | | | | 1.5–2.4(7H, m, OC 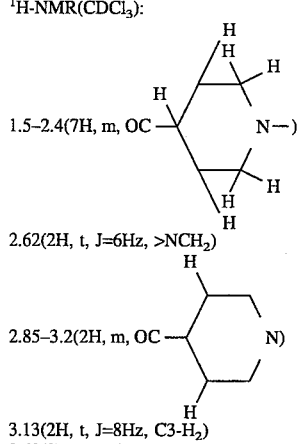 N—) |
| | | | | | | 2.62(2H, t, J=6Hz, >NCH₂) |
| | | | | | | 2.85–3.2(2H, m, OC N) |
| | | | | | | 3.13(2H, t, J=8Hz, C3-H₂) 3.63(2H, t, J=6Hz, CH₂O) 4.15(2H, t, J=8Hz, C2-H₂) |

TABLE 2-continued
| Example | A | B | m, n, X | $R^1$ | $R^2$ | IR(vcm$^{-1}$) $^1$H-NMR(δppm) |
|---|---|---|---|---|---|---|
| | | | | | | 5.05(2H, s, C5-CH$_2$) 5.41(1H, s, >CH) 6.75–7.5(15H, m, phenyl, C4, C6-H, imidazole) 8.0–8.4(1H, m C7-H) |
EXAMPLES 17–29
Compounds of the formula (XX)
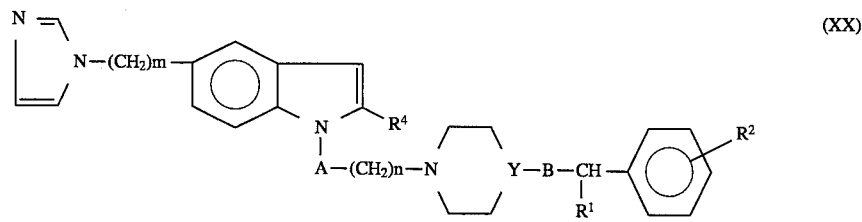
(XX)
wherein $R^1$, $R^2$, A, B, Y, m, and n are as shown in Table 3, were produced according to the methods of Examples 3 and 6 above. The IR and $^1$H-NMR of the obtained compounds are as shown in Table 3.

TABLE 3

| Example | A | B | m, n, Y | R¹ | R² | R⁴ | IR(νcm⁻¹) ¹H-NMR(σppm) |
|---|---|---|---|---|---|---|---|
| 17 | — | —CH₂CH₂O— | 0, 2, >N— | φ | —H | —H | IR(Nujol): 3400 <br> ¹H-NMR(CDCl₃) <br> 1.7–3.0(14H, m, —CH₂CH₂N⟨piperazine⟩NCH₂—) <br> 3.66(2H, t, J=7Hz, —CH₂OCH⟨ ⟩) <br> 4.22(2H, t, J=7Hz, >N—CH₂CH₂—) <br> 5.38(1H, s, —OCH(φ)(φ)) <br> 6.5–8.0(18H, m, indole H, imidazole H, phenyl H) |
| 18 | —CH₂CH₂O— | — | 0, 2, >CH— | —H | —H | —H | IR(Nujol): 3400 <br> ¹H-NMR(CDCl₃) <br> 1.0–3.0(13H, m, —CH₂—piperidine-CH₂—) <br> 3.2–4.0(4H, m, —CH₂OCH₂—) <br> 4.32(2H, t, J=6Hz, >NCH₂—) <br> 6.3–7.9(13H, m, indole H, imidazole H, phenyl H) |
| 19 | — | — | 0, 3, >N— | φ | —H | —H | IR(Nujol): 3350 <br> ¹H-NMR(CDCl₃) <br> 0.9–1.5(2H, m, —CH₂—CH₂—piperidine N) <br> 2.4–2.55(10H, m, —CH₂N⟨piperidine⟩N) <br> 4.25(1H, s, =CHφ₂) <br> 4.26(2H, t, J=6Hz, NI—CH₂) <br> 6.57(1H, m, C3-H) |

TABLE 3-continued

| Example | A | B | m, n, Y | R$^1$ | R$^2$ | R$^4$ | IR(vcm$^{-1}$)<br>$^1$H-NMR(δppm) |
|---|---|---|---|---|---|---|---|
| 20 | — | — | 0, 3, >CH— | —H | —H | —H | 7.84(1H, s, N-CH=N imidazole)<br>7.0–7.7(16H, m, C2, C4, C6, C7-H, phenyl, N-CH=CH imidazole)<br>IR(Neat): 3400<br>$^1$H-NMR(CDCl$_3$):<br>1.1–2.4(9H, m, —CH$_2$CH$_2$N piperidine-CH-CH$_2$)<br>2.4–3.2(6H, m, —CH$_2$CH$_2$N piperidine)<br>4.22(2H, t, J=6Hz, N1—CH$_2$)<br>6.53(1H, m, C3-H)<br>6.9–7.75(11H, m, C2, C4, C6, C7-H, phenyl, N-CH=CH imidazole)<br>7.82(1H, s, N-CH=N imidazole) |
| 21 | — | — | 1, 3, >N— | —φ | —H | —H | IR(Neat): 3350<br>$^1$H-NMR(CDCl$_3$) |

TABLE 3-continued

| Example | A | B | m, n, Y | R¹ | R² | R⁴ | IR(νcm⁻¹) ¹H-NMR(δppm) |
|---|---|---|---|---|---|---|---|
| | | | | | | | 1.7–2.8(12H, m, —CH₂CH₂N⟨⟩N—) <br> 4.15(2H, t, J=6Hz, >NCH₂—) <br> 4.2(1H, s, >NCH(φ)(φ)) <br> 5.13(2H, s, —CH₂Im) <br> 6.3–7.7(18H, m, imidazole H, indole H, phenyl H) |
| 22 | — | — | 1, 3, >CH— | —H | —H | —H | IR(Neat): 3350 <br> ¹H-NMR(CDCl₃) <br> 1.0–3.1(15H, m, —CH₂CH₂N⟨⟩CH₂—) <br> 4.15(2H, t, J=6Hz, >NCH₂) <br> 5.13(2H, s, —CH₂Im) <br> 6.4–7.7(18H, m, imidazole H, indole H, phenyl H) |
| 23 3HCl | — | — | 1, 3, >N— | —φ | —H | —CO₂H | IR(Nujol): 1700, 1460, 1380 <br> ¹H-NMR(DMSO-d₆) <br> 1.50–4.40(12H, m, —NCH₂CH₂N⟨⟩NCH) <br> 4.20–4.90(3H, m, —NCH₂, —NCH) <br> 5.53(2H, s, C₅—CH₂) <br> 7.00–8.10(17H, m, indole H, imidazole H, φ₂H) <br> 9.47(1H, s, —CO₂H) |
| 24 2HCl | — | — | 1, 3, >CH— | —H | —H | —CO₂H | IR(Nujol): 3400, 1710, 1450 <br> ¹H-NMR(DMSO-d₆) <br> 1.30–4.35(15H, m, —NCH₂CH₂N⟨⟩CH₂φ) <br> 4.35–4.90(2H, m, NCH₂) <br> 5.55(2H, s, C₅—CH₂) <br> 7.05–8.05(12H, m, indole H, imidazole H, φ-H) |

TABLE 3-continued

| Example | A | B | m, n, Y | R¹ | R² | R⁴ | IR(νcm⁻¹) ¹H-NMR(δppm) |
|---|---|---|---|---|---|---|---|
| 25 (CO₂H)₂ | — | — | 0, 3, >CH— | H | H | —CH₃ | IR(KBr): 3400, 1620<br>¹H-NMR(DMSO-d₆)<br>1.2–3.6(15H, m, —C$\underline{H_2}$CH₂N–cyclohexyl-CH₂—)<br>2.45(3H, s, —CH₃)<br>4.25(2H, t, J=7Hz, >NC$\underline{H_2}$CH₂—)<br>6.3(1H, s, indole 3-position H)<br>7.0–8.3(13H, imidazole H, indole 4,6,7-H, phenyl H) |
| 26 3/2(CO₂H)₂ | — | — | 0, 2, >N— | –φ | H | H | IR(KBr): 3200, 1620<br>¹H-NMR(DMSO-d₆)<br>2.3–3.7(10H, m, —CH₂N–piperazine-Nφ)<br>4.2–4.8(3H, m, >NC$\underline{H_2}$CH₂—, —C$\underline{H}$(φ)₂)<br>6.5–8.0(18H, m, indole H, imidazole H, phenyl H)<br>8.5(3H, br, CO₂$\underline{H}$ × 3) |
| 27 (CO₂H)₂ | — | — | 0, 2, >CH | H | H | H | IR(KBr): 3400, 1620<br>¹H-NMR(DMSO-d₆, δppm)<br>1.2–2.0(5H, m, —C$\underline{H_2}$CH–cyclohexyl-C$\underline{H_2}$—)<br>2.5–3.6(8H, m, —C$\underline{H_2}$N–cyclohexyl-CH₂-φ)<br>4.65(2H, t, t, J=7Hz, >NC$\underline{H_2}$CH₂—)<br>6.5–8.3(15H, indole H, phenyl H, imidazole H, CO₂$\underline{H}$ × 2) |
| 28 | — | — | 0, 3, >N— | –φ | H | —CH₃ | IR(Nujol): 3400, 1620,<br>¹H-NMR(DMSO-d₆, δppm) |

TABLE 3-continued

| Example | A | B | m, n, Y | R¹ | R² | R⁴ | IR(νcm⁻¹)<br>¹H-NMR(σppm) |
|---|---|---|---|---|---|---|---|
| | | | | | | | 1.7–3.8(15H, m, —CH$_2$CH$_2$N(piperidine)N—, —CH$_3$)<br>4.20(2H, t, J=7Hz, >N—C$\underline{H_2}$CH$_3$)<br>4.40(1H, s, —C$\underline{H}$(φ)(φ))<br>6.30(1H, s, indole 3-position H)<br>7.0–8.4(19H, indole 4,6,7-position H, imidazole H, phenyl H, CO$_2$$\underline{H}$ × 3) |
| 29<br>3/2(CO$_2$H)$_2$ | — | —CH$_2$CH$_2$O— | 0, 3, >N— | -φ | —H | CH$_3$ | IR(Nujol): 3400, 1620<br>¹H-NMR(DMSO-d$_6$)<br>1.5–3.2(14H, m, —CH$_2$CH$_2$N(piperidine)NCH$_2$—)<br>2.45(3H, s, —CH$_3$)<br>3.65(2H, t, J=7Hz, —C$\underline{H_2}$OCH)<br>4.25(2H, t, J=7Hz, >NC$\underline{H_2}$CH—)<br>5.50(1H, s, —C$\underline{H}$(φ)(φ))<br>5.80(3H, br, CO$_2$$\underline{H}$ × 3)<br>6.30(1H, s, indole 3-position H)<br>7.0–8.5(16H, m, indole H, imidazole H, phenyl H) |

EXAMPLES 30–42

Compounds of the formula (XXI)

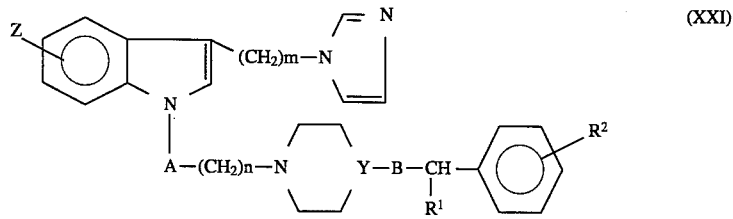

wherein $R^1$, $R^2$, A, B, Y, Z, m, and n are as shown in Table 4, were produced according to the methods of Examples 4 and 5 above. The IR and $^1$H-NMR of the obtained compounds are as shown in Table 4.

TABLE 4

| Example | A | B | Z | m, n, Y | $R^1$ | $R^2$ | IR($vcm^{-1}$) $^1$H-NMR($\sigma$ppm) |
|---|---|---|---|---|---|---|---|
| 30 | — | — | 6-$CO_2$Na | 1, 3, >CH | H | H | IR(Nujol): 1580<br>$^1$H-NMR(DMSO-$d_6$)<br>0.8–3.0(15H, m, —$CH_2CH_2$N〈piperidine〉$CH_2$—)<br>4.25(2H, br, >N—$\underline{CH_2}$—)<br>5.35(2H, s, —$\underline{CH_2}$ Im)<br>6.75–8.20(12H, indole H, imidazole H, phenyl H) |
| 31 | — | — | 5-$CO_2$Na | 1, 3, >N— | -φ | —H | IR(Nujol): 1620<br>$^1$H-NMR(DMSO-$d_6$)<br>1.6–2.7(12H, m, —$CH_2CH_2$N〈piperazine〉N—)<br>4.0–4.4(3H, br, —C$\underline{H}$(φ)(φ), >N$\underline{CH_2}$—)<br>5.30(2H, s, —$\underline{CH_2}$Im)<br>6.7–8.3(17H, m, indole H, imidazole H, phenyl H) |
| 32 | — | — | 5-$CO_2$Na | 1, 3, >CH | H | H | IR(KBr method): 1620<br>$^1$H-NMR(DMSO-$d_6$)<br>0.8–3.0(15H, m, —$CH_2CH_2$N〈piperidine〉$CH_2$—)<br>4.15(2H, br, >N$\underline{CH_2}$—)<br>5.32(2H, s, —$\underline{CH_2}$Im)<br>6.6–8.3(12H, m, indole H, imidazole H, phenyl H) |
| 33 | — | — | 5-$CO_2$Na | 2, 3, >N— | -φ | —H | IR(KBr method): 1580<br>$^1$H-NMR(DMSO-$d_6$)<br>1.4–2.7(12H, m, —$CH_2CH_2$N〈piperazine〉N—)<br>3.15(2H, t, J=7Hz, —$\underline{CH_2}CH_2$Im)<br>3.8–4.0(5H, m, —$CH_2\underline{CH_2}$Im, N$\underline{CH_2}CH_2CH_2$—, —C$\underline{H}$(φ)(φ))<br>6.8–8.3(17H, m, indole H, imidazole H, phenyl H) |
| 34 | — | — | 5-$CO_2$Na | 2, 3, >CH— | —H | H | IR(KBr method): 1580<br>$^1$H-NMR(DMSO-$d_6$) |

TABLE 4-continued

| Example | A | B | Z | m, n, Y | R¹ | R² | IR(νcm⁻¹) ¹H-NMR(δppm) |
|---|---|---|---|---|---|---|---|
| | | | | | | | 1.0–3.0(15H, m, —CH₂CH₂N⟨C₆H₁₀⟩CH₂—) 3.21(2H, t, J=7Hz, —C$\underline{H}$₂CH₂Im) 3.9–4.5(4H, m, —CH₂C$\underline{H}$₂Im, >NC$\underline{H}$₂CH₂—) 6.7–8.3(12H, m, indole H, imidazole H, phenyl H) |
| 35 | — | —CH₂CH₂O— | 5-CO₂Na | 2, 3, >N— | -φ | H | IR(Nujol): 1580 ¹H-NMR(DMSO-d₆) 1.4–2.8(14H, m, —CH₂CH₂N⟨⟩NCH₂—) 3.15(2H, t, J=7Hz, —C$\underline{H}$₂CH₂Im) 3.48(2H, t, J=7Hz, —C$\underline{H}$₂OCH(φ)(φ)) 3.7–4.5(4H, m; —CH₂C$\underline{H}$₂Im, >NC$\underline{H}$₂CH₂CH₂—) 5.45(1H, s, —OC$\underline{H}$(φ)(φ)) 6.7–8.3(17H, m, indole H, imidazole H, phenyl H) |
| 36 | — | — | H | 1, 3, >N— | -φ | H | IR(Neat): 3380 ¹H-NMR(CDCl₃) 1.7–2.8(12H, m, —CH₂CH₂N⟨⟩N—) 4.13(2H, t, J=7Hz, >NC$\underline{H}$₂CH₂—) 4.22(1H, s, —CH(φ)(φ)) 5.22(2H, s, —C$\underline{H}$₂Im) 6.8–7.7(18H, indole H, phenyl H, imidazole H) |
| 37 | — | — | H | 1, 3, >CH— | —H | H | IR(Neat): 3350 ¹H-NMR(CDCl₃) 1.0–3.1(15H, m, —CH₂CH₂N⟨C₆H₁₀⟩CH₂—) 4.15(2H, t, J=7Hz, >NC$\underline{H}$₂CH₂—) 5.25(2H, s, —C$\underline{H}$₂Im) 6.9–7.7(13H, m, indole H, imidazole H, phenyl H) |
| 38 | — | — | H | 2, 3, —CH< | H | H | IR(Neat): 1500 ¹H-NMR(CDCl₃) 1.0–3.0(15H, m, —CH₂CH₂N⟨C₆H₁₀⟩CH₂—) 3.17(2H, t, J=7Hz, —C$\underline{H}$₂CH₂Im) 3.9–4.4(4H, m, —CH₂C$\underline{H}$₂Im, >NC$\underline{H}$₂CH₂CH₂—) 6.5–7.6(13H, indole H, imidazole H, phenyl H) |
| 39 3/2 | — | — | 6-CO₂H | 1, 3, >N— | -φ | H | IR(Nujol): 3300, 1640 ¹H-NMR(DMSO-d₆) |

TABLE 4-continued

| Example | A | B | Z | m, n, Y | R$^1$ | R$^2$ | IR(vcm$^{-1}$) $^1$H-NMR(σppm) |
|---|---|---|---|---|---|---|---|
| (CO$_2$H)$_2$ | | | | | | | 1.5–3.2(12H, m, —CH$_2$CH$_2$N⟨N⟩) |
| | | | | | | | 4.2–4.7(3H, br, >NCH$_2$—, C$\underline{H}$⟨φ/φ⟩) |
| | | | | | | | 5.50(2H, s, —C$\underline{H_2}$Im) |
| | | | | | | | 6.30(4H, br, CO$_2$H × 4) |
| | | | | | | | 7.0–8.3(17H, m, indole H, imidazole H, phenyl H) |
| 40 3/2 (CO$_2$H)$_2$ | — | — | 6-CO$_2$H | 1, 2, >N— | -φ | —H | IR(Nujol): 3400, 1640 $^1$H-NMR(DMSO-d$_6$) |
| | | | | | | | 1.5–3.2(10H, m, —CH$_2$N⟨N—⟩) |
| | | | | | | | 4.2–4.7 (3H, br, >NCH$_2$—, C$\underline{H}$⟨φ/φ⟩) |
| | | | | | | | 5.50(2H, s, —C$\underline{H_2}$Im) |
| | | | | | | | 6.30(4H, br, CO$_2$H × 4) |
| | | | | | | | 7.0–8.6(17H, m, indole H, imidazole H, phenyl H) |
| 41 3/2 (CO$_2$H)$_2$ | — | —CH$_2$CH$_2$O— | 6-CO$_2$H | 1, 3, >N— | -φ | H | IR(Nujol): 3400, 1640 $^1$H-NMR(DMSO-d$_6$) |
| | | | | | | | 1.5–3.7(m, 16H, —CH$_2$CH$_2$N⟨NCH$_2$CH$_2$O—⟩) |
| | | | | | | | 4.0–4.5(2H, br, >NCH$_2$—) |
| | | | | | | | 5.50(3H, s, —CH$_2$Im, —C$\underline{H}$⟨φ/φ⟩) |
| | | | | | | | 7.0–8.5(21H, m, indole H, phenyl H, imidazole H, CO$_2$H × 4) |
| 42 (CO$_2$H)$_2$ | — | — | 6-CO$_2$H | 1, 2, >C— | —H | —H | IR(Nujol): 3400, 1640 $^1$H-NMR(DMSO-d$_6$) |
| | | | | | | | 1.0–3.5(13H, m, —CH$_2$N⟨⟩—CH$_2$—) |
| | | | | | | | 4.2–4.7(2H, br, >N—CH$_2$—) |
| | | | | | | | 5.10(3H, br, CO$_2$H × 3) |
| | | | | | | | 5.50(2H, s, —C$\underline{H_2}$Im) |
| | | | | | | | 6.7–8.2(12H, m, indole H, imidazole H, phenyl H) |

Other imidazole compounds of the formula (I) are:
1-[4-(4-benzhydryl-1-piperazinyl)butyl]-3-(1H-imidazol-1-ylmethyl) -1H-indole-6-carboxylic acid, 1-[3-(4-(p-chlorobenzyl)-1-piperazinyl)propyl]- 3-(1H-imidazol-1-ylmethyl)-1H-indole-6-carboxylic acid, 1-[3-(4-benzyl-1-piperidino)propyl]-3-(1H-imidazol-1-ylmethyl)-1H-indole-6-carboxylic acid, 1-[3-(4-benzhydryloxy-1-piperidino)propyl]-3-(1H-imidazol-1-ylmethyl)-1H-indole-6-carboxylic acid, and 1-[3-(4-benzhydryl-1-piperidino)propyl]-5-(1H-imidazol-1-ylmethyl)indoline.

REFERENCE EXAMPLE 1

Synthesis of 5-(1H-imidazol-1-yl)indoline (1) 1-Acetyl-5-(1H-imidazol-1-yl)indoline 1-Acetyl-5-bromoindoline (30.0 g) was suspended in DMF (300 ml), and imidazole (25.5 g), K$_2$CO$_3$ (34.5 g), copper powder (1.9 g), and KF (1.7 g) were added thereto, followed by stirring at 150° C. for 20 hours. After cooling, chloroform was added, and insoluble matters were filtered off, after which the filtrate was washed with water and saturated brine, and dried over anhydrous sodium sulfate. The solvent was distilled away under reduced pressure. The resultant crystals were filtered off to give 23.0 g of crystals.

IR (Nujol, vcm$^{-1}$) 1660 $^1$H-NMR (DMSO-d$_6$, δ ppm) 2.17 ( 3H, s, —COCH$_3$), 3.18 (2H, t, J=8 Hz, C$_3$—H), 4.12 ( 2H, t, J=8 Hz, C$_2$—H), 6.90–8.30 (6H, m, phenyl, imidazole)

To 1-acetyl-5-(1H-imidazol-1-yl)indoline (23.0 g) as obtained in (1) was added 6N HCl (230 ml), and the mixture was stirred at 120° C. for 4 hours. After cooling, chloroform and water were added, and the mixture was adjusted to pH 8–9 with 4N NaOH, followed by extraction with chloroform. The organic layer was washed with saturated brine, and dried over anhydrous sodium sulfate. The solvent was distilled away under reduced pressure to give 18.7 g of the crude title compound 5-(1H-imidazol-1-yl)indoline as an oil.

IR (Neat, vcm$^{-1}$) 2950, 2850, 1510 $^1$H-NMR (CDCl$_3$, δ ppm) 3.07 (2H, m, C$_3$—H), 3.20 (1H, s, >NH), 3.62 (2H, m, C$_2$—H), 6.59 (1H, d, J=8 Hz, C$_7$—H), 6.80–7.30

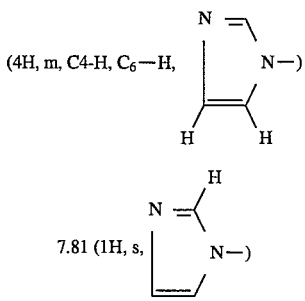

REFERENCE EXAMPLE 2

5-(1H-Imidazol-1-ylmethyl)indoline (1) 1-Acetyl-5-chloromethylindoline

To 1-acetylindoline (20.0 g) in conc. hydrochloric acid (400 ml) w added 35% formalin (9.86 ml), and the mixture was stirred at 57° C. for 1 hour while blowing in hydrogen chloride gas. The mixture was stirred for further 3 hours after the blowing was stopped. After cooling, the reaction mixture was poured into water (400 ml), and the resultant insoluble matters were filtered off, and the filtrate was extracted with chloroform (4 times). The organic layer was washed with saturated brine, and dried over anhydrous sodium sulfate. The solvent was distilled away under reduced pressure to give 22 g of a brown oily substance (crude).

$^1$H-NMR (CDCl$_3$, δ ppm) 2.23 (3H, s, COCH$_3$), 3.17

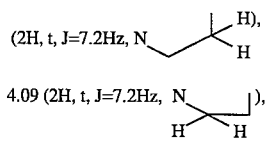

4.58 (2H, s, C$_5$—CH$_2$), 6.90–7.45 (2H, m, C$_4$, C$_6$—H), 8.19 (1H, br-d, J=7.8 Hz, C$_7$—H)

(2) 1-Acetyl-5-(1H-imidazol-1-ylmethyl )indoline

The crude 1-acetyl-5-chloromethylindoline (22.0 g) as obtained in (1) was dissolved in acetone (150 ml), and imidazole (21.7 g) and potassium carbonate (43.5 g) were added thereto. The mixture was stirred at room temperature for 15 hours. The insoluble matters were filtered off, and the solvent was distilled away under reduced pressure. Water was added to the residue, and it was extracted twice with chloroform. The residue was purified by silica gel column chromatography (Daisogel 300 g, elution; CHCl$_3$—CHCl$_3$/MeOH=50/1–20/1) to give 12.5 g of crystals.

IR (Nujol, vcm$^{-1}$) 2920, 2850, 1650, 1450 $^1$H-NMR (CDCl$_3$, δ ppm) 2.20 (3H, s, N—COCH$_3$), 3.15 (2H, br-t, J=8.4 Hz,

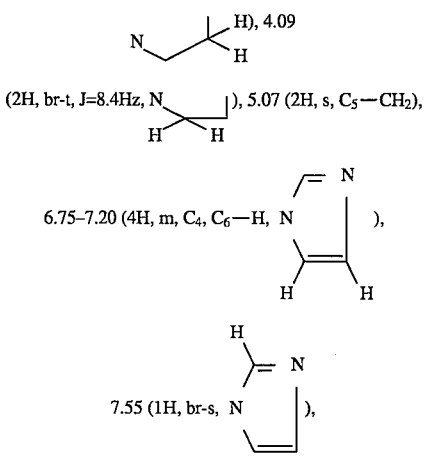

8.20 (1H, br-d, C$_7$-H)

1-Acetyl-5-(1H-imidazol-1-ylmethyl)indoline (6.5 g) as obtained in (2) was dissolved in 6N HCl (130 ml), and the mixture was stirred while heating at 70° C. for 6 hours. The reaction mixture was concentrated under reduced pressure, and 2N NaOH was added to the residue to make the solution alkaline, followed by extraction with chloroform (3 times). The organic layer was washed with saturated brine, and dried over anhydrous sodium sulfate. The solvent was distilled away under reduced pressure to give 4.6 g of the title compound 5-(1H-imidazol- 1-ylmethyl)indoline as crystals.

IR (Nujol, vcm$^{-1}$) 1610, 1500, 1460, 1380 $^1$H-NMR (CDCl$_3$, δ ppm) 3.00

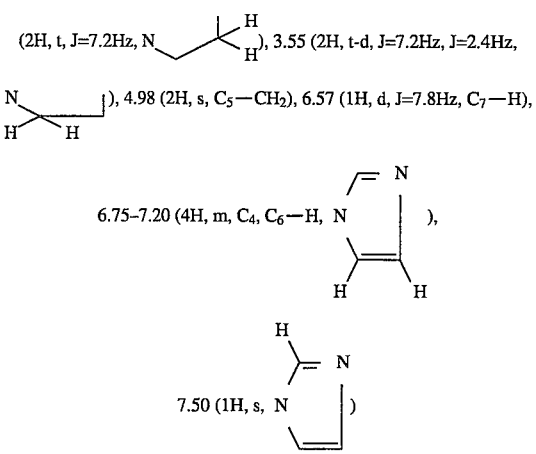

REFERENCE EXAMPLE 3

Synthesis of 5-(1H-imidazol-1-yl )-1H-indole 5-(1H-Imidazol-1-yl)indoline (3.0 g) was dissolved in DMF (30 ml), and sodium hydride (1.3 g) was added thereto. The mixture was stirred at room temperature for 24 hours.

After extraction with ethyl acetate, the extract was washed with water and dried over anhydrous sodium sulfate. The solvent was distilled away, and the residue was purified by silica gel column chromatography (ethyl acetate) to give 1.6 g of the title compound 5-(1H-imidazol-1-yl)-1H-indole.

IR (Nujol, vcm$^{-1}$) 3450 $^1$H-NMR (CDCl, δ ppm) 6.50 (1H, br-s, indole C$_3$—H), 6.8–8.3 (7H, m, indole C$_2$, C$_4$, C$_6$, C$_7$—H), 11.30 (1H, br-s, NH)

REFERENCE EXAMPLE 4

Synthesis of 6-ethoxycarbonyl-3-(1H-imidazol-1-ylmethyl)-1H-indole

To a mixed solution of dioxane (50 ml), glacial acetic acid (50 ml), and 35% formaldehyde (27 ml, 317 mM) was added about 50% dimethylamine (28 ml, 317 mM) under ice-cooling, and the mixture was stirred at said temperature for 30 minutes. 6-Ethoxycarbonyl-1H-indole (6.0 g, 3.17 mM) was added thereto, and the mixture was allowed to become ambient temperature, followed by stirring for 2 hours. After neutralization with a saturated solution of sodium hydrogencarbonate, the water layer was saturated with NaCl, and extracted with ethyl acetate. The solvent was dried and distilled away under reduced pressure. The residue was dissolved in xylen (150 ml), added with imidazole (10.8 g, 158.5 mM), and stirred at 100° C. for 10 hours. Thereto was added chloroform, and the organic layer was washed with water and dried over anhydrous sodium sulfate. The solvent was distilled away under reduced pressure to give 6.0 g of the title compound 6-ethoxycarbonyl-3-(1H-imidazol-1-ylmethyl)-1H-indole as crystals.

IR (Nujol, vcm$^{-1}$) 1700 $^1$H-NMR (DMSO-d$_6$, δ ppm) 1.33 (3H, t, J=7 Hz, CH$_2$C$\underline{H_3}$), 4.32 (2H, q, J=7 Hz, —C$\underline{H_2}$CH$_3$), 5.35

(2H, s, 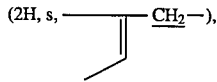 CH$_2$—), 6.7–8.3 (7H, m, indole H, imidazole H), 11.3 (1H, br, >NH)

What is claimed:

1. An imidazole derivative of the formula (I)

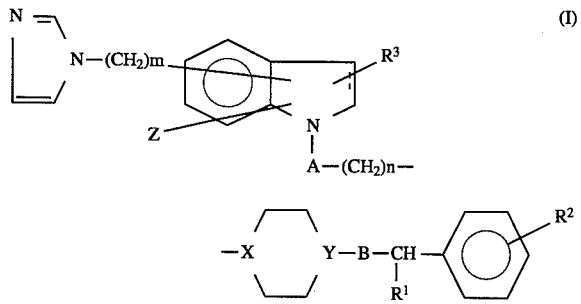

(I)

wherein R$^1$ is hydrogen atom or aryl selected from the group consisting of phenyl, tolyl and xylyl which is unsubstituted or substituted on the benzene ring by hydrogen, nitro or alkoxy having 1 to 4 carbon atoms, R$^2$ is hydrogen atom, halogen, lower alkyl having 1 to 4 carbon atoms, or lower alkoxy having 1 to 4 carbon atoms, R$^3$ is hydrogen atom or lower alkyl having 1 to 4 carbon atoms, A is a direct bond, —CO—, —CH$_2$CO—, —CONH—, —COCH$_2$O—, or alkyleneoxy wherein the alkylene has 1 to 5 carbon atoms, B is a direct bond, —O—, alkylene having 1 to 5 carbon atoms, or alkyleneoxy wherein the alkylene has 1 to 5 carbon atoms, X and Y are both nitrogen atoms or either of them is nitrogen atom and the other is CH, Z is hydrogen atom, carboxyl, or alkoxy carbonyl wherein the alkoxy has 1 to 4 carbon atoms, m and n are 0 or an integer of 1–4, and the broken line means a single bond or double bond, or a pharmacologically acceptable salt thereof.

2. The imidazole derivative as claimed in claim 1 which is selected from the group consisting of
   1-[3-(4-benzhydryl-1-piperazinyl)propyl]-3-(1H-imidazol-1-ylmethyl)-1-H-indole-6-carboxylic acid,
   1-[2-(4-benzhydryl-1-piperazinyl)ethyl]-3-(1H-imidazol-1-ylmethyl)-1H-indole-6-carboxylic acid,
   1-[4-(4-benzhydryl-1-piperazinyl)butyl]-3-(1H-imidazol-1-ylmethyl)-1H-indole-6-carboxylic acid,
   1-[3-(4-benzhydryl-1-piperidino)propyl]-3-(1H-imidazol-1-ylmethyl)-1H-indole-6-carboxylic acid,
   1-[3-(4-benzhydryloxyethyl-1-piperazinyl)propyl]-3-(1H-imidazol-1-ylmethyl)-1H-indole-6-carboxylic acid,
   1-[3-(4-(p-chlorobenzyl)-1-piperazinyl)propyl]-3-(1H-imidazol-1-ylmethyl)-]-1H-indole-6-carboxylic acid,
   1-[3-(4-benzyl-1-piperidino)propyl]-3-(1H-imidazol-1-ylmethyl)-1H-indole-6-carboxylic acid,
   1-[3-(4-benzhydryloxy-1-piperidino)propyl]-3-(1H-imidazol-1-ylmethyl)-1H-indole-6-carboxylic acid,
   1-[3-(4-benzhydryl-1-piperazinyl)propyl]-3-(1H-imidazol-1-ylmethyl)-1H-indole-5-carboxylic acid,
   1-[3-(4-benzhydryl-1-piperazinyl)propyl]-5-(1H-imidazol-1-ylmethyl)indoline, and
   1-[3-(4-benzhydryl-1-piperidino)propyl]-5-(1H-imidazol-1-ylmethyl)indoline, or a pharmacologically acceptable salt thereof.

3. A pharmaceutical composition containing the imidazole derivative as claimed in claim 1, or a pharmacologically acceptable salt thereof, and a pharmacologically acceptable carrier.

4. A method for the prophylaxis or treatment of a disease induced by thromboxane A$_2$ or histamine selected from the group consisting of bronchial asthma, allergy, nephritis, thrombosis, cerebral apoplexy, myocardial infarction, angina pectoris, and ischemic cerebral circulatory disorder, which comprises administering to a patient an amount effective for prophylaxis or treatment of said disease, of the imidazole derivative as claimed in claim 1 or a pharmacologically acceptable salt thereof.

* * * * *